(12) United States Patent  
Maschke

(10) Patent No.: US 7,289,842 B2  
(45) Date of Patent: Oct. 30, 2007

(54) SYSTEM FOR MEDICAL EXAMINATION OR TREATMENT

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 442 days.

(21) Appl. No.: 10/946,455

(22) Filed: Sep. 21, 2004

(65) Prior Publication Data

US 2005/0101859 A1     May 12, 2005

(30) Foreign Application Priority Data

Sep. 22, 2003   (DE)   ................. 103 43 808

(51) Int. Cl.  
*A61B 6/00*   (2006.01)
(52) U.S. Cl. ............... 600/478; 600/466; 600/467; 600/476
(58) Field of Classification Search ............. 600/407, 600/473–475, 476–479, 437, 309, 424, 342  
See application file for complete search history.

(56) References Cited

U.S. PATENT DOCUMENTS

| 5,430,476 | A | * | 7/1995 | Hafele et al. ............... 348/70 |
| 5,935,075 | A | * | 8/1999 | Casscells et al. ........... 600/474 |
| 6,134,003 | A | * | 10/2000 | Tearney et al. ............. 356/479 |
| 6,501,551 | B1 | * | 12/2002 | Tearney et al. ............. 356/477 |

FOREIGN PATENT DOCUMENTS

| EP | 0 964 644 B1 | 12/1999 |
| WO | WO98/57580 | 12/1998 |
| WO | WO99/42179 | 8/1999 |
| WO | WO 01/11409 A2 | 2/2001 |

OTHER PUBLICATIONS

Brezinski, M.E.; Tearney, G.J.; Weissman, N.J.; Boppart, S.A.; Bouma, B.E.; Hee, M.R.; Weyman, A.E.; Swanson, E.A.; Southern, J.F.; Fujimoto, J.G., "Assessing atherosclerotic plaque morphology: comparison of optical coherence tomography and high frequency intravascular ultrasound," Heart, 1997; 77:397-403.*

(Continued)

*Primary Examiner*—Lynda Jasmin  
*Assistant Examiner*—James Talman

(57) ABSTRACT

The invention relates to a medical investigation and/or treatment system comprising:

a catheter system, comprising a catheter (1, 7, 9), with a first sensor (4, 11) of an imaging system for optical coherence tomography with an optical fiber via which the light is directed and is radiated in the area of a catheter tip introduced into an area to be investigated, via which fiber reflection light is directed from an illuminated investigation area to a first image processing unit (22), a second sensor (3, 8, 10) of an intravascular ultrasound imaging system to transmit and receive sound pulses which are fed as an electrical signal to a second image processing unit (23), und at least one display unit (24) for presenting the images of the first and second image processing unit (22, 23).

20 Claims, 3 Drawing Sheets

OTHER PUBLICATIONS

Pan, Y.; Lankenau, E.; Welzel, J.; Birngruber, R.;Engelhardt, R., Optical Coherence—Gated Imaging of Biological Tissues, IEEE Journal of Selected Topics in Quantum Electronics, vol. 2, No. 4, pp. 1029-1034, 1996.*

Brezinski, M.; Fujimoto, J; "Optical Coherence Tomography: High-Resolution Imaging in Nontransparent Tissue", IEEE Journal of Selected Topics in Quantum Electronics, vol. 5, No. 4, pp. 1185-1192, 1999.*

Patwari, P.; Weissman, N.; Boppart, S.; Jesser, C.; Stamper, De.;Fujimoto, J.;Brezinski, M., "Assessment of Coronary Plaque With Optical Coherence Tomography and High-Frequency Ultrasound," The Americal Journal of Cardiology, 2000;85:641-644.*

* cited by examiner

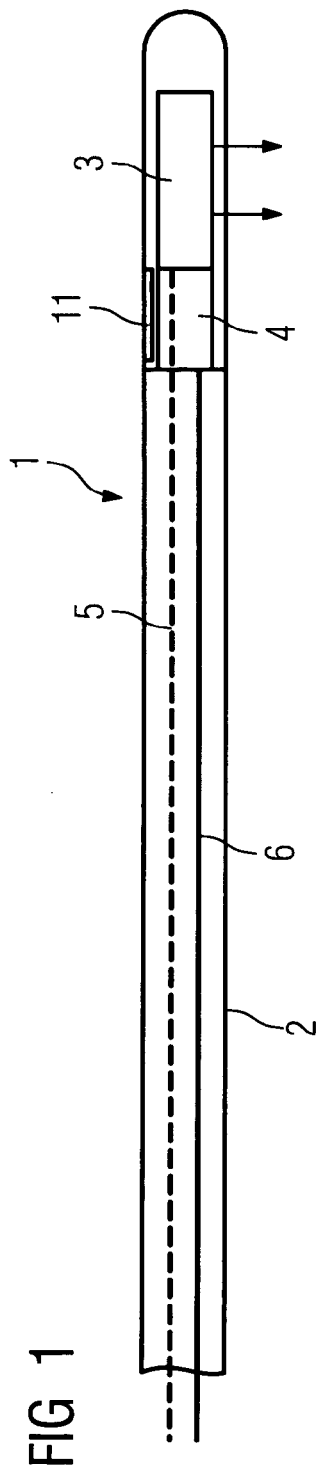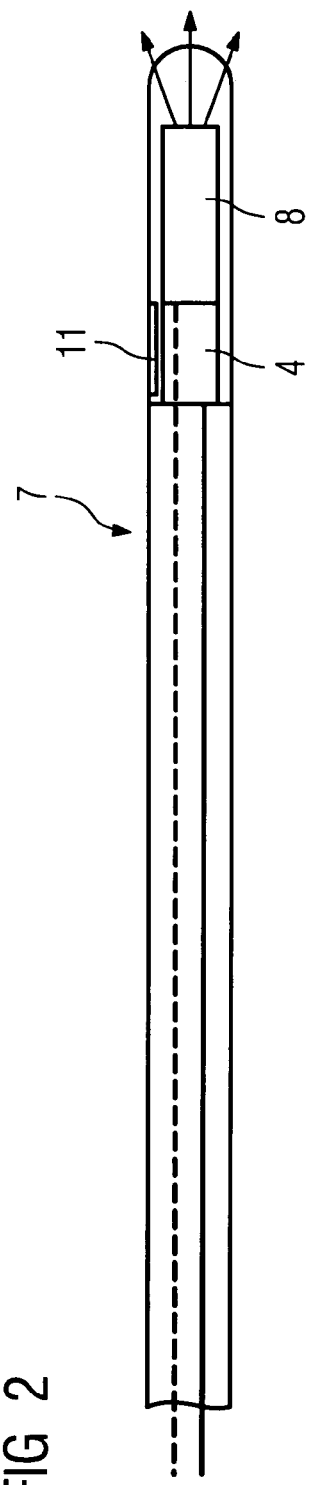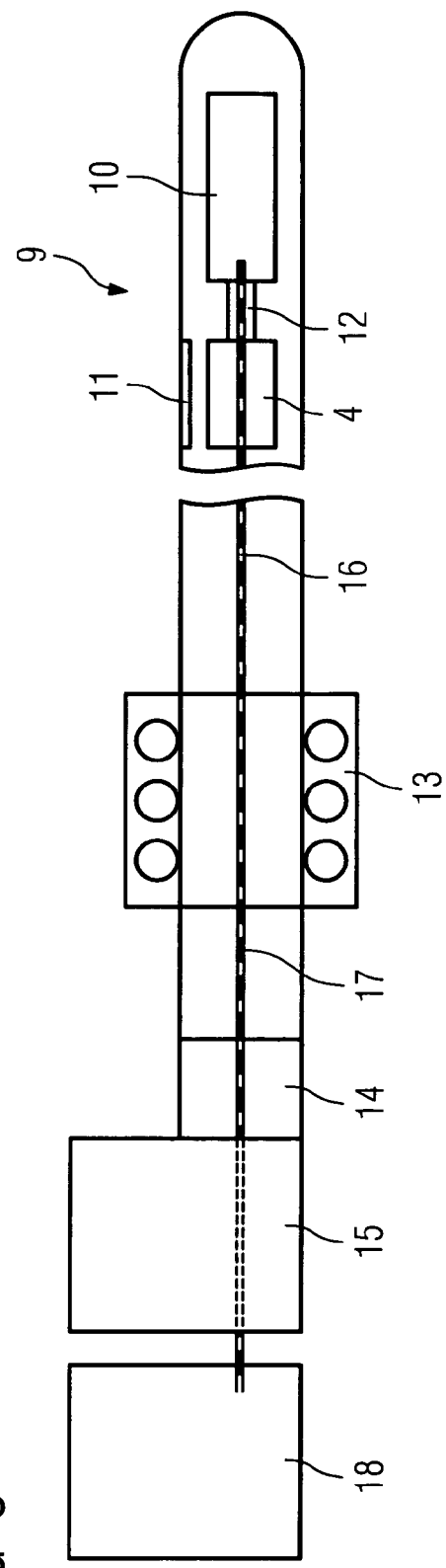

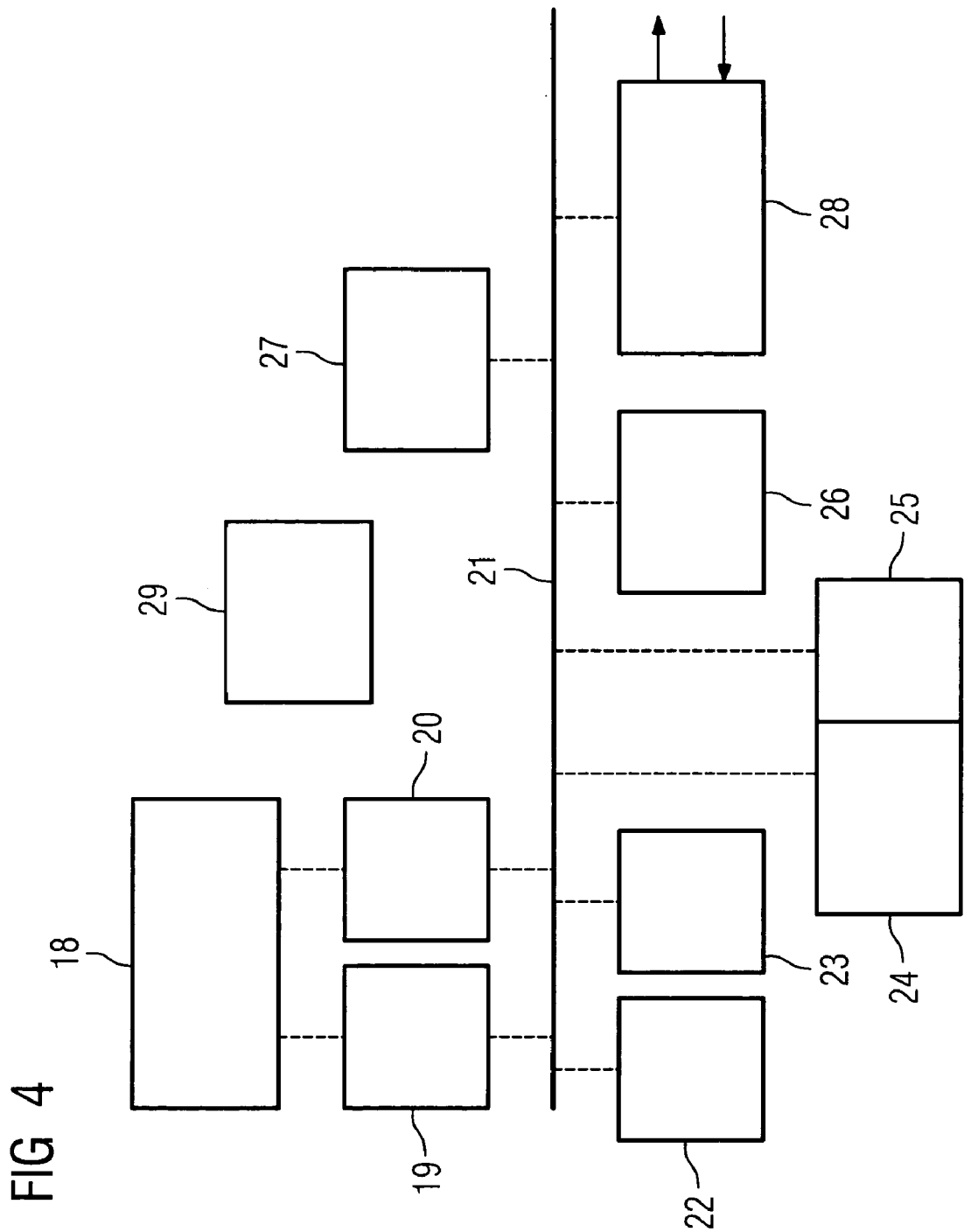

SYSTEM FOR MEDICAL EXAMINATION OR TREATMENT

CROSS REFERENCE TO RELATED APPLICATIONS

This application claims priority to the German application No. 10343808.4, filed Sep. 22, 2003 and which is incorporated by reference herein in its entirety.

FIELD OF INVENTION

The invention relates to a medical investigation and/or treatment system.

BACKGROUND OF INVENTION

Vascular conditions, especially heart attacks, are among the most frequent illnesses resulting in death. These are caused by diseases of the coronary arteries (arterial sclerosis). In such conditions deposits, referred to as arterial plaque, result in "blocking" of coronary arteries. The latest knowledge shows that the danger of suffering a heart attack does not depend primarily on the reduction of the diameter of the arteries. It is far more a matter of whether the thin protective layer which covers the arteriosclerotic deposits is stable. If this layer breaks down, blood platelets are released which completely close off the artery within a short time, thereby causing a heart attack.

SUMMARY OF INVENTION

Previously coronary arteries have been investigated within the framework of coronary angiography essentially by means of heart catheter investigations with contrast agents under x-ray control. The disadvantage of this method however is that only the artery diameter usable by the blood flow or the restriction are shown as a silhouette. This means that the method does not allow any information to be provided about the arteriosclerotic deposits such as their thickness or the presence of inflammation processes.

In another method a intravascular ultrasound catheter (IVUS) is introduced into the coronary artery with the aid of a guide wire and subsequently withdrawn from the artery manually or by a motor-driven pulling device at a defined speed. This method is described for example in DE 198 27 460 A1. The catheter provides ultrasound images of the coronary arteries, where the artery wall is mostly shown in a 360° cross-section. These images provide important medical information about the deposits, e.g. centers of inflammation and the thickness of the deposit. However the general disadvantage of ultrasound images is that their resolution is limited.

With a further new method which has already been trialed and is described in WO 01/11409 A2 a intravascular catheter for Optical Coherence Tomography (OCT) which uses infrared light, is introduced into the coronary artery and subsequently with-drawn from the artery manually or by a motor-driven pulling device at a defined speed. The images of the OCT system de-liver additional medical information about arteriosclerotic plaque. The advantage of this solution is that structures in the vicinity of the surface of the artery can be resolved to a very high level of detail, in some cases microscopic tissue images are possible. The disadvantage of this method lies in the low level of resolution of tissue further down.

An object of the invention is to create a system for medical examination or treatment which possesses an optimum diagnostic image quality.

This object is achieved by the claims.

The invention is based on the knowledge that an optimal diagnostic image quality can be achieved with a system which combines the advantages of intravascular ultrasound investigation (IVUS) with the advantages of optical coherence tomography (OCT). The medical investigation and treatment system in accordance with invention is optimized for artery investigations and removes the above-mentioned disadvantages of the two known methods.

The medical investigation and treatment system in accordance with invention in which both methods are combined into one system leads to a good resolution in the lower-lying areas of the arteries and simultaneously to a very good resolution in the local area of the arteries. This is especially of advantage in the investigation of arteriosclerotic plaque.

The improved image quality facilitates the diagnosis of coronary arteries, in addition to arteriosclerotic plaque implanted stents can also be better checked, so that any necessary medical measures can be initiated in good time.

The medical investigation and/or treatment system in accordance with the invention also allows better diagnosis with other diseases of the arteries.

In accordance with the invention the catheter system comprises a catheter with a first sensor for optical coherence tomography and a second sensor of an intravascular ultrasound imaging system. Since the two sensors are combined into one catheter, its dimensions are smaller compared to two separate catheters. This means that the catheter can be made especially small which is of advantage in relation to the investigations to be performed. The first and the second sensor are each connected to an image processing device which generates an image from the reflected light of the optical coherence tomography or from the electrical signal which is obtained from the ultrasound signal. These images can be presented on the display unit.

To further improve the medical investigation and/or treatment system in accordance with the invention there can be provision for the images of the first and the second image processing unit to be shown together on the display unit. The investigator therefore sees the image generated by OCT and by IVUS simultaneously. The OCT image of the first image recording system in particular enables precise detection of the tissue structures in the area of the surface of the artery. The intravascular ultrasound image also allows tissue lower down in the artery to be investigated. Accordingly the benefits of both known methods can be expediently employed in the system in accordance with the invention.

In accordance with a further development of the medical investigation and/or treatment system in accordance with the invention there can be provision for the central area of the image displayed on the display unit to show a section of the image created by means of optical coherence tomography and the outer area to display a section they created by means of intravascular ultrasound imaging.

From the two images of the first and the second image processing unit a single image is created in accordance with the invention consisting of sections of both images. For the central area of the new, combined image a section of the image generated by means of OCT is used, since OCT delivers the best results in this area of investigation. For the outer area of the combined image a section of the image generated by means of intravascular ultrasound is used which delivers higher quality images of the artery walls.

There can be provision for the central area or of the combined image displayed on the display unit to be an essentially circular section of the image generated by optical coherence tomography. The combined image is made up of a circular inner image section and an outer section surrounding the circular section.

To generate the combined common image from the images of the first and the second image processing unit an image fusion unit can be provided. As well as the combination of an outer and an inner image section it is also possible to generate the common combined image by overlaying the images of the first and the second image processing unit.

In order to generate an accurately detailed image of the artery it is worthwhile registering the images producing the common image of the first and the second imaging processing unit with each other. The technical term registration designates images which feature the same phase relation. This ensures that the center image section and the outer image section surrounding it are displayed with the same phase so that the images coincide at the common edges.

The advantage of the solution in accordance with the invention lies in its simple registration since the two sensors are located in a single catheter.

To obtain as realistic as possible an image of the artery to be investigated there can be provision for the sensor of the Intravascular ultrasound imaging system to be arranged in the front area of the catheter tip and directed to the side and/or diagonally forwards.

The sensor of the optical coherence tomography can usefully be directed to the side. Furthermore, seen from the tip of the catheter, it can be arranged behind the sensor of the intravascular ultrasound imaging system. In this case the IVUS sensor covers the area of the artery lying in front of or to the side of the catheter, the OCT sensor covers the side area.

To achieve a layout which is as simple as possible there can be provision for the sensor of the optical coherence tomography and the sensor of the intravascular imaging system to be driven via a common drive shaft. With a catheter constructed in this way there is no need for a separate drive for the second sensor. It makes particular sense for the optical fiber to be the drive shaft. In this case the optical fiber on one hand serves to direct a light beam which is radiated into the investigation area, at the same time the reflection light is fed back via the optical fiber and the optical fiber serves as a drive shaft for the OCT sensor, if necessary for both sensors.

To simplify the image processing of the medical investigation and/or treatment system there can be provision for the sensor of the optical coherence tomography and the sensor of the intravascular ultrasound imaging system to be able to be driven at the same speed. The two sensors can then be controlled so that the images that they deliver are automatically in the same phase, doing away with the need for expensive computational registration. In accordance with a further development of the invention there can however also be provision for the OCT sensor and the IVUS sensor to be operated at different speeds, if necessary with an intermediate microdrive.

As an alternative to the drive described using the glass fiber drive shaft, to generate the rotational movement of the IVUS sensor an electrical micromotor or one driven by an external magnetic field can be provided. This layout can be useful for particular applications if different sensor speeds are required.

BRIEF DESCRIPTION OF THE DRAWINGS

Further advantages and details of the invention are produced by the exemplary embodiments described below as well as being illustrated by the diagrams. These show:

FIG. 1 a first exemplary embodiment of a catheter of an investigation and treatment system in accordance with the invention;

FIG. 2 a second exemplary embodiment of a catheter of an investigation and treatment system in accordance with the invention;

FIG. 3 a third exemplary embodiment of a catheter of an investigation and treatment system in accordance with the invention;

FIG. 4 the principal layout of the investigation and/or treatment system in accordance with invention;

DETAILED DESCRIPTION OF INVENTION

Figure 5A:
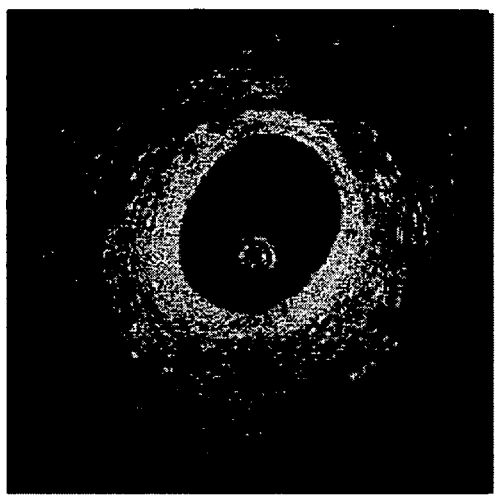
FIG. 5a an OCT image with very high resolution in the local area.

FIG. 1 shows a catheter 1, essentially consisting of a catheter envelope 2, an IVUS sensor 3 arranged in the area of the catheter tip which is part of an intravascular ultrasound imaging system and an OCT sensor 4 which is part of an imaging system for optical coherence tomography. The catheter envelope accommodating the sensors 3, 4 is transparent for ultrasound.

The IVUS sensor 3 is embodied so that the ultrasound is radiated and received in an approximately sideways direction. Since the IVUS sensor 3 is revolving at high speed, which can be 1,800 RPM, it delivers a 360° comprehensive cross-sectional image of the artery to be investigated. The reflected received sound waves are converted by the IVUS sensor 3 into electrical signals which are forwarded via a signal line 5 to a signal interface and thence to a pre-processing unit and an image processing unit.

The OCT sensor 4 is also directed to the side so that it generates a continuous image of the artery to be investigated. The side of the OCT sensor 4 features a window 11 in a cutout for the infrared light radiated by the sensor. The reflected light is directed via a signal line 6 embodied as a glass fiber line to the signal interface and thence to a pre-processing unit and an image processing unit.

For the catheter 1 shown in FIG. 1 the sensors 3, 4 are mechanically connected to each other in such a way that they rotate at the same speed.

FIG. 2 shows a second exemplary embodiment of a catheter 7 which differs from the catheter 1 shown in FIG. 1 in that the ultrasound sensor 8 radiates diagonally forwards. The other components of the catheter 7 correspond to those of catheter 1 of FIG. 1. Catheter 7 delivers an image which looks some-what different and which also takes account of the areas of the artery lying in front of catheter 7, whereas catheter 1 radiates precisely at right angles to its longitudinal axis and to the artery.

FIG. 3 shows a exemplary embodiment of a catheter 9 which is part of the medical investigation and/or treatment system. Unlike in the previous exemplary embodiments the IVUS sensor 10 und the OCT sensor 4 are not connected directly to each other but through an intermediate drive shaft 12. In addition a microdrive, not illustrated, can be provided so that the IVUS sensor 10 and the OCT sensor 4 can be driven at different speeds. Like the catheters shown in FIGS. 1 and 2, catheter 9 features a window on the side for OCT sensor 4.

At the end of catheter 9 opposite the catheter tip a drive unit 13 is arranged to move the catheter. The drive unit 13 allows the catheter 9 to be withdrawn at a constant speed for example.

Behind the drive unit 13 catheter 9 is connected via a mechanical connection system 14 to a rotational drive 15 shown schematically. The signal lines 16, 17 of the IVUS sensor 10 and the OCT sensor 4 are connected to a signal interface 18.

FIG. 4 shows the basic structure of the medical investigation and/or treatment system. A catheter 1, 7 or 9 shown in FIGS. 1-3 is connected to the signal Interface 18. For reasons of hygiene and to protect against infections the catheters are designed for single use and are changed for each investigation or treatment. The OCT and IVUS signals transmitted via the signal lines of the catheter are directed via the signal Interface 18 to the pre-processing unit 19 for optical coherence tomography or the pre-processing unit for intravascular ultrasound 20 to a data bus 21. Via the data bus 21 the recorded image signals are fed to an image processing unit 22 for OCT or an image processing unit 23 for IVUS. In the image processing units 22, 23 the signals recorded by the sensors are converted so that they can be shown as images.

A display unit 24 is used to present the OCT and IVUS images which in the simplest case can be embodied as one monitor. The display unit 24 can also be embodied so that it consists of a number of individual monitors to enable the OCT and IVUS images to be observed separately. The display unit 24 obtains the image data over a data bus 21 from the image processing units 22, 23. An I/O unit 25 is connected to the display unit 24 and can be used to enter information. In particular it can influence the presentation of the image or images shown on the display unit 24. The I/O unit 25 can be embodied as a keyboard or an operator console and is also connected to data bus 21.

An image fusion unit 26 is used to produce a composite image from the separate images generated by the signals of the OCT sensor or the IVUS sensor. In the simplest case "image fusions" is merely an overlaying of the individual images from OCT and IVUS. Preferably however a common and combined investigation image is produced by combining a specific image section of the IVUS image and a second image section of the OCT image. Expediently the two image sections can be embodied to coincide, so that the OCT section fits precisely into the free area of the IVUS image. In this way the optimal area of both images is included for the generating the combined image. The IVUS image features very high resolution in the areas deeper in the artery. The OCT image has a very high resolution in the local area, meaning that even microscopic images are possible.

The OCT image section and the IVUS image section can be merged using the appropriate image processing programs so that no separating line or contour can be detected. These tasks will also be handled by the image fusion unit 26.

An image data store 27 which stores the individual images sequentially is connected to the data bus 21. In specific cases it can be necessary to record further parameters such as the phase relation or the speed of rotation of the sensor in addition to the image information. The distance covered by the catheter can also be recorded and this is especially easy to achieve if the catheter is withdrawn by the drive unit 13.

As can be seen from FIG. 4, an interface 28 is also connected to the data bus 21 which enables patient data and image data to be exchanged with other computers, investigation devices and databases.

The components of the investigation and treatment system illustrated in FIG. 4 are linked via lines not shown in the diagram to a power supply unit 29.

FIG. 5a shows an OCT image of which the outstanding feature is its very high resolution in the local area. Structures close to the surface of the artery can be resolved in detail, even microscopic tissue images are possible.

Figure 5B:
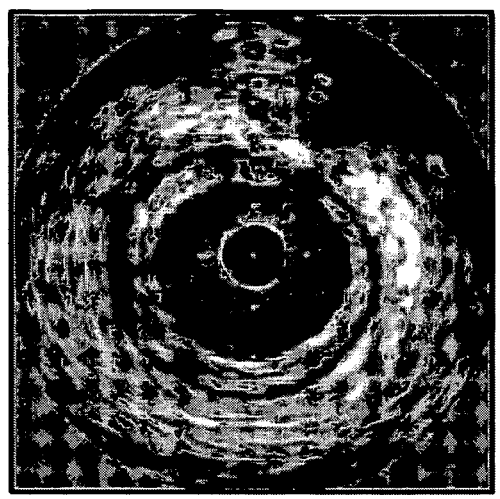
FIG. 5b an IVUS he image with good resolution in the deeper arterial layers.

FIG. 5b shows an IVUS image with lower resolution in the local area, but far better resolution of the tissue layers deeper down. On the basis of this image the thickness of the arteriosclerotic deposits can be determined for example.

Figure 5C:
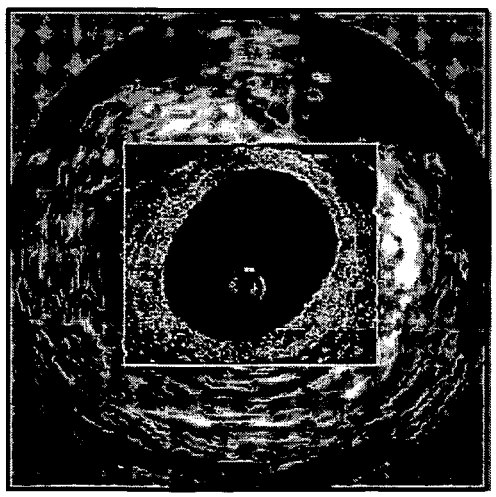
FIG. 5c a composite image combined from the OCT image and the IVUS-image.

FIG. 5c shows a composite image made up of the IVUS image from FIG. 5b and the OCT image from FIG. 5a. This image processing operation is executed by image fusion unit 26, in which case the inner, central section of the OCT image has been combined with the matching, outer area of the IVUS image.

Figure 5D:
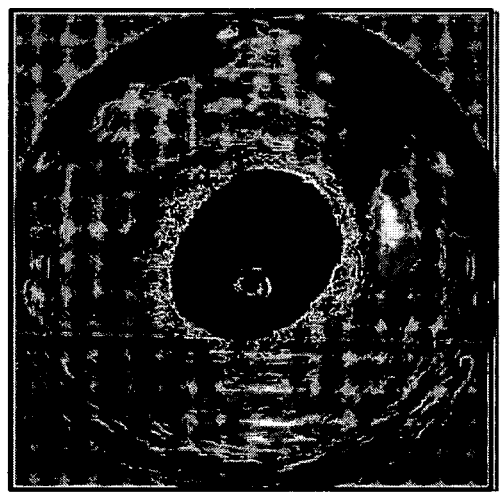
FIG. 5d a second composite image.

FIG. 5d shows a second composite image which, like the image shown in FIG. 5c, has been generated from image sections of the OCT image and the IVUS image. After the image fusion further image processing was undertaken to conceal the joint edges. The two fused images 5c und 5d produce an optimal presentation in the local area and in the tissue layers further down.

In practice the medical investigation and/or treatment system can also be used so that the area of interest is initially searched with the IVUS image, then a switch can be made to the combined image.

The invention claimed is:

1. A system for medical examination or treatment, comprising:
    a catheter of a catheter system, the catheter comprising:
        a first sensor of an imaging system for optical coherence tomography having an optical fiber for directing and emitting light into an area adjacent to a catheter tip introduced into an examination area and for directing reflected light from the illuminated examination area to a first image processing device; and
        a second sensor of an intravascular ultrasound imaging system for transmitting and receiving sound pulses fed to a second image processing device as electrical signals;
    and
    at least one display device for outputting of images processed by the first and the second image processing device
    wherein the display device:
    displays an image generated by the first image processing device in a center area on a screen of the display device, wherein the center area is a circular section of the image generated by the first image processing device, and
    displays an image generated by the second image processing device in an outer area on the screen of the display device and wherein the display device jointly merges and displays the images processed by the first and the second image processing devices.

2. The system according claim 1, further comprising an image merging device for generating the joint image using the images generated by the first and the second image processing devices.

3. The system according to claim 1, wherein the display device is adapted to display the images generated by the first and the second image processing devices as a joint image, wherein one of the images superposes the other image at least partially.

4. The system according to claim 1, wherein the second sensor is arranged in a front area of the catheter tip and focused to the side or diagonally forwards with regard to a longitudinal axis of the catheter.

5. The system according to claim 1, wherein the second sensor is arranged in a front area of the catheter tip and focused diagonally forwards with regard to a longitudinal axis of the catheter.

6. The system according to claim 1, wherein the first sensor is focused to the side or diagonally forwards with regard to a longitudinal axis of the catheter.

7. The system according claim 1, wherein the first sensor is arranged after the second sensor with regard to a direction defined by a longitudinal axis of the catheter with the catheter tip as a starting point.

8. The system according to claim 1, wherein the first and the second sensor are movable by a common driving shaft.

9. The system according to claim 8, wherein the optical fiber is the driving shaft.

10. The system according claim 8, wherein the first and the second sensor are operated using the same rotational speed for each sensor.

11. The system according to claim 8, wherein the first and the sensor are operated using different rotational speeds for each sensor.

12. The system according to claim 11, further comprising a micro gear for operating the sensors at the different rotational speeds.

13. The system according to claims 1, further comprising a micro drive motor for generating a rotational movement of the second sensor.

14. The system according to claim 13, wherein the micro drive motor is powered electrically.

15. The system according to claim 13, wherein the micro drive motor is powered by an external magnetic field.

16. The system according to claim 1, further comprising a drive unit for moving the catheter.

17. The system according to claim 16, wherein the drive unit is adapted to move the catheter at a constant speed.

18. The system according to claim 1, wherein a joint image is formed using a first and a second image generated by the first and the second image processing device respectively, wherein the first and the second image are recorded together.

19. The system according to claim 18, wherein the first and the second image are in-phase.

20. A method of examining a patient comprising introducing a catheter tip of a catheter into an examination area of the patent, the catheter comprising:

a first sensor of an imaging system for optical coherence tomography having an optical fiber for directing and emitting light into an area adjacent to a catheter tip introduced into an examination area and for directing reflected light from the illuminated examination area to a first image processing device; and a second sensor of an intravascular ultrasound imaging system for transmitting and receiving sound pulses fed to a second image processing device as electrical signals;

displaying an image generated by the first image processing device in a center area on a screen of the display device, wherein the center area is a circular section of the image generated by the first image processing device, and displaying an image generated by the second image processing device in an outer area on the screen of the display device merging the images from the first and second image processing devices to form a joint image and displaying the joint image.

* * * * *